United States Patent
Lin et al.

(10) Patent No.: US 9,523,032 B2
(45) Date of Patent: Dec. 20, 2016

(54) MEDICAL CONTRAST AGENT MADE OF MICROBUBBLES CONTAINING FLUORESCENT GOLD NANOCLUSTERS

(71) Applicant: CHUNG YUAN CHRISTIAN UNIVERSITY, Taoyuan County (TW)

(72) Inventors: Cheng-An J. Lin, Taoyuan County (TW); Walter Hong-Shong Chang, Taoyuan County (TW); Chih-Hsien Lee, Taoyuan County (TW); Wen-Kai Chuang, Taoyuan County (TW)

(73) Assignee: CHUNG YUAN CHRISTIAN UNIVERSITY, Taoyuan (TW)

( * ) Notice: Subject to any disclaimer, the term of this patent is extended or adjusted under 35 U.S.C. 154(b) by 228 days.

(21) Appl. No.: 14/468,355

(22) Filed: Aug. 26, 2014

(65) Prior Publication Data
US 2014/0360981 A1    Dec. 11, 2014

Related U.S. Application Data

(62) Division of application No. 13/018,442, filed on Feb. 1, 2011, now abandoned.

(51) Int. Cl.
*A61B 5/055* (2006.01)
*C09K 11/58* (2006.01)
*A61K 49/22* (2006.01)
*C09K 11/08* (2006.01)
*A61K 49/00* (2006.01)

(52) U.S. Cl.
CPC .......... *C09K 11/58* (2013.01); *A61K 49/0091* (2013.01); *A61K 49/223* (2013.01); *C09K 11/08* (2013.01); *A61K 49/0017* (2013.01)

(58) Field of Classification Search
CPC ................................................. A61K 49/0017
See application file for complete search history.

(56) References Cited

U.S. PATENT DOCUMENTS

| 4,844,882 A * | 7/1989 | Widder .................. A61B 8/481 424/9.52 |
| 5,409,688 A | 4/1995 | Quay |
| 6,352,683 B1 * | 3/2002 | ten Cate ................ A61K 41/00 424/450 |
| 7,591,452 B2 | 9/2009 | Kohama et al. |
| 2009/0156932 A1 | 6/2009 | Zharov |

FOREIGN PATENT DOCUMENTS

JP    2010139289    6/2010

OTHER PUBLICATIONS

Xie et al. (J. Am. Chem. Soc. 2009, 131, 888-889 and S1-S6).*
Retnakumari et al. (Nanotechnol. 2010, 21, 055103, p. 1-12).*
Lin et al. (ACSNano 2009, 3, 395-401, Supporting information 1-34).*
American Chemical Society 2009, vol. 3, pp. 395-401.
Synthesis of Fluorescent Metallic Nanoclusters toward Biomedical Application: Recent Progress and Present Challenges;Cheng-An J. Lin, Chih-Hsien Lee, Jyun-Tai Hsieh, Hsueh-Hsiao Wang, Jimmy K. Li, Ji-Lin Shen, Wen-Hsiung Chan, Hung-I Yeh, Walter H. Chang;Journal of Medical and Biological Engineering, 29(6): 276-283.
Advance of US microbubble contrast media; Lin Ling-bo, GUOKang-he , Ma Yu-xiang, et al.;J Med Imaging vol. 16 No. 4 2006;p. 411-423.
Soft Matter, vol. 4, pp. 2350-2359,2008.
16th European Symposium on Ultrasound Contrast Imaging, Jan. 20-21, 2011.
Handbook of Optical Coherence Tomography, pp. 409-427, Mar. 7, 2006.
Microfluidic Assembly of Monodisperse, Nanoparticle-Incorporated Perfluorocarbon Microbubbles for Medical Imaging and Therapy, Seo et al. (Langmuir 2010, 26, 13855-13860).
Protein-Directed Synthesis of Highly Fluorescent Gold Nanoclusters, Xie et al. (J. Am. Chem. Soc. 2009, 131, 888-889).

* cited by examiner

*Primary Examiner* — Michael G Hartley
*Assistant Examiner* — Melissa Perreira
(74) *Attorney, Agent, or Firm* — CKC & Partners Co., Ltd.

(57) ABSTRACT

A medical contrast agent made of microbubbles containing Au nanoclusters is provided. The shell of the microbubbles contains fluorescent Au nanocluster-albumin complex, and the core contains air or fluorocarbons. The method for preparing the microbubbles is also disclosed.

9 Claims, 7 Drawing Sheets

Step 220

MEDICAL CONTRAST AGENT MADE OF MICROBUBBLES CONTAINING FLUORESCENT GOLD NANOCLUSTERS

RELATED APPLICATIONS

This application is a divisional application of co-pending U.S. patent application Ser. No. 13/018,442 for the same title filed on Feb. 1, 2011, the content of which is hereby incorporated by reference in its entirety.

BACKGROUND

Technical Field

The disclosure relates to a diagnostic agent. More particularly, the disclosure relates to a contrast agent or a medical contrast medium used in biomedical imaging.

Description of Related Art

A medical contrast agent is a substance used to enhance the contrast of structures of fluids within the body in medical imaging. Microbubbles contrast agents are used to aid the sonographic detection. The bubbles are composed of tiny amounts of air, nitrogen or perfluorocarbon surrounded by proteins, lipids, or polymer shells. The density on the interface between the gas in the bubble and the surrounding liquid strongly scatters and reflects the ultrasound back to the probe. This process of backscattering gives the liquid with these bubbles a high signal, which can be seen in the resulting image.

Two kinds of microbubbles have been approved by Food and Drug Administration (FDA). One has an albumin shell and octafluoropropane gas core. The other has a lipid/galactose shell and an air core.

SUMMARY

Accordingly, this invention tried to modify the microbubbles above to prepare a multifunctional contrast agent for various biomedical imaging.

In one aspect, the present invention is directed to a medical contrast agent made of microbubbles containing fluorescent Au nanoclusters, each microbubble comprises a core filled with air or fluorocarbons surrounding by a shell. The shell comprises a plurality of Au nanocluster-albumin complex, and the structure of the each complex comprises a fluorescent Au nanocluster surrounded by a layer of a first albumin. Furthermore, the complex may further comprise a protecting ligand between the fluorescent Au nanocluster and the layer of the first albumin.

According to an embodiment, the shell can further comprise a second albumin to dilute the concentration of the Au nanocluster-albumin complex.

The first and the second albumins above can be a serum albumin, an ovalbumin, or a storage albumin.

In another aspect, the present invention is directed to a method of preparing microbubbles containing fluorescent Au nanoclusters. A $Au^{3+}$ solution and a first albumin solution are mixed to form a mixing solution. $Au^{3+}$ is reduced by adding a base into the mixing solution to form the Au nanocluster-albumin complex, wherein the Au nanocluster is surrounded by a layer of the first albumin. The Au nanocluster-albumin complex is dispersed in water or phosphate buffered saline to form a dispersed solution. The dispersed solution is sonicated at an ultrasound intensity of about 11-24 watts for about 1-3 minutes to form microbubbles.

According to another embodiment, a $Au^{3+}$ solution and a protecting ligand solution are mixed to form a mixing solution. $Au^{3+}$ is reduced by adding a reductant into the mixing solution to form the Au nanocluster-ligand complex, wherein the Au nanocluster is surrounded by a layer of the ligand. The Au nanocluster-ligand complex solution and an albumin solution are mixed together to form Au-albumin complexes, in which a layer of albumin surrounds each of the Au-ligand complexes. Then, the Au nanocluster-ligand complex and an albumin are dispersed in water or phosphate buffered saline to form a dispersed solution. The dispersed solution is sonicated at an ultrasound intensity of about 11-24 watts for about 1-3 minutes to form microbubbles.

The forgoing presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

DETAILED DESCRIPTION

Figure 1A:
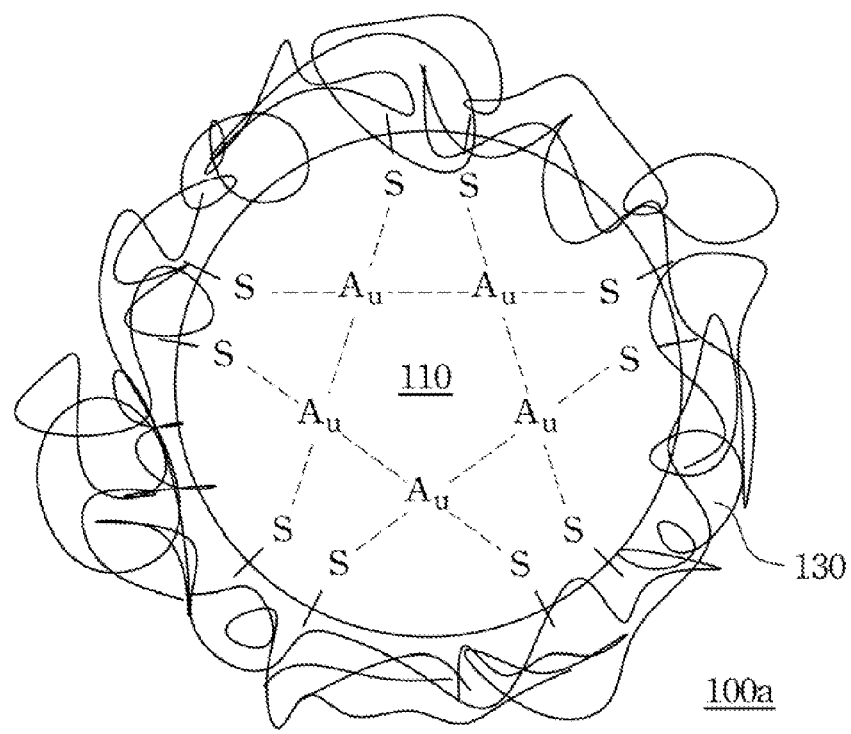
FIGS. 1A and 1B are cross-sectional diagrams of Au NC-albumin complex.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Structure of Microbubbles

According to an embodiment of this invention, the shell of the microbubbles is mainly composed of plural fluorescent Au nanocluster (NC)-albumin complex, and further albumins can be added therein. The core of the microbubbles can be air or fluorocarbons, such as octafluoropropane. The diameter of the microbubbles is about 0.5-20 μm. For the purpose of the medical use in human body, the diameter of the microbubbles is better about 0.5-6 μm.

Figure 1B:
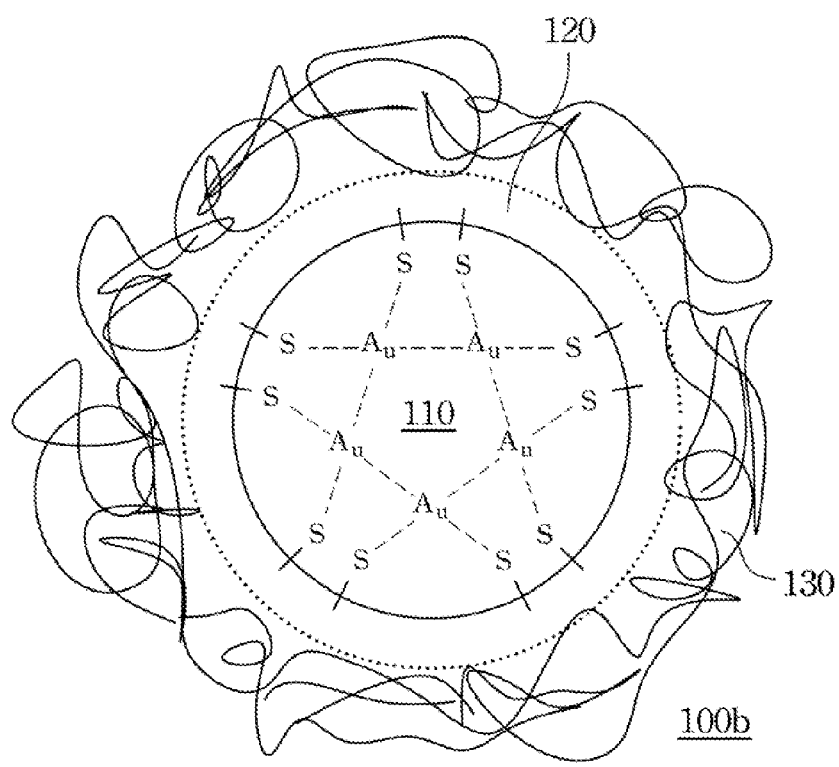

FIGS. 1A and 1B are cross-sectional diagrams of Au NC-albumin complex described above. The Au NC-protein complex can be a 2-layer structure shown in FIG. 1A or a 3-layer structure shown in FIG. 1B. In FIG. 1A, the 2-layer structure of the Au nanocluster-albumin complex 100a is a fluorescent Au nanocluster (abbreviated as NC below) 110 capped with albumins (noted as AuNC@albumin in the below). In FIG. 1B, the core of the 3-layered Au nanocluster-albumin complex 100b is fluorescent Au nanocluster 110, the middle layer is a protecting ligand (abbreviated as ligand below) 120 having at least a thiol (—SH) functional group, and the outer layer is albumins 130 (noted as AuNC@ligand_albumin in the below). The diameter of the Au nanocluster is about 1.9±0.8 nm, and hence the Au nanocluster can emit fluorescence having wavelength 640±90 nm.

The albumins 130 in FIG. 1A and the ligand 120 in FIG. 1B usually use —SH group to encapsulate the Au nanocluster. The interaction between the outer albumins 130 and the middle ligand 120 in FIG. 1B usually is electrostatic interaction, such as hydrogen bonding or ionic bonding.

The albumin above refers generally to any protein that is water soluble. Examples of albumin include serum albumin, ovalbumin in egg white, or other storage albumins in seeds of some plants. The serum albumin above can be human serum albumin (HSA) or bovine serum albumin (BSA), for example. It is better to use HSA to avoid allergy reaction when the microbubbles are used in human body. The ligand above can be dihydrolipoic acid (DHLA), glutathione, tiopronin, meso-2,3-dimercaptosuccunic acid, phenylethylthiolate, dodecanethiol, or mercaptoundecanol, for example.

Figure 1C:
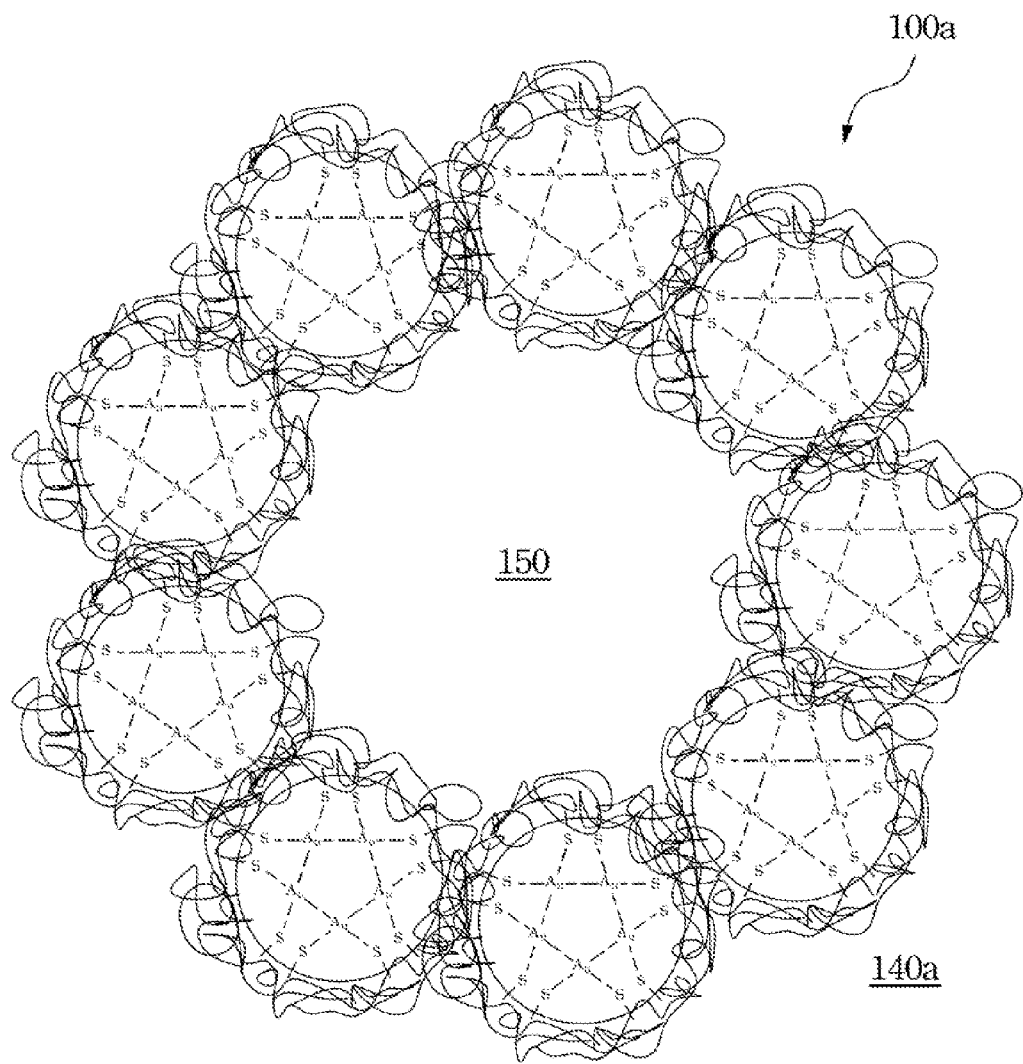
FIGS. 1C and 1D are cross-sectional diagrams of a microbubble according to embodiments of this invention.
Figure 1D:
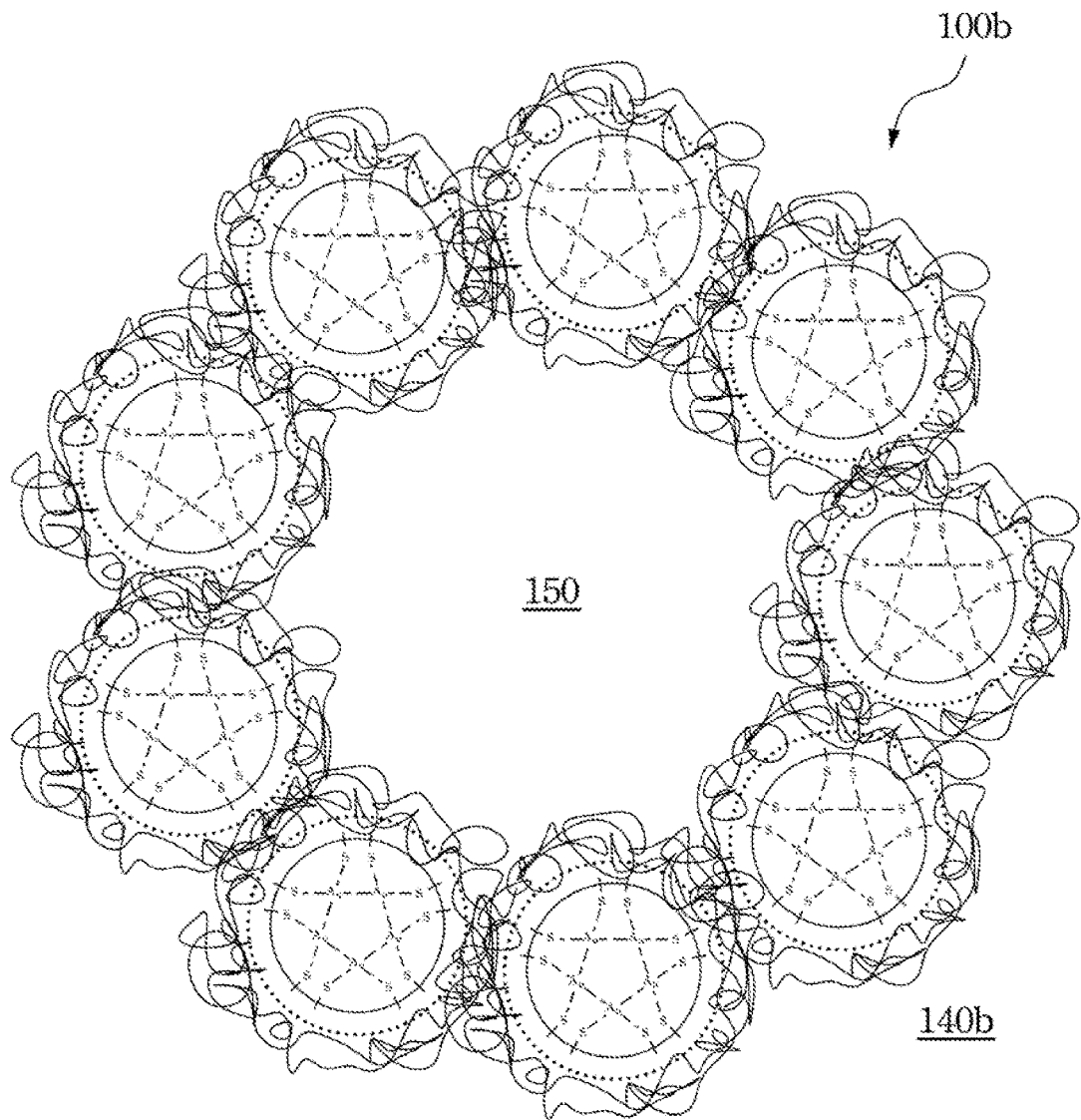

For example, FIGS. 1C and 1D are cross-sectional diagrams of microbubble according to embodiments of this invention. In FIG. 1C, the shell of the microbubble 140a is mainly composed of the Au nanocluster-albumin complex 100a having 2-layer structure. In FIG. 1D, the shell of the microbubble 140b is mainly composed of the Au nanocluster-albumin complex 100b having 3-layer structure. The core 150 in both FIGS. 1C and 1D can be filled with air or fluorocarbons.

Accordingly, the fluorescent Au nanocluster can emit fluorescence and be integrated in the microbubbles. Therefore, the microbubbles contain the fluorescent Au nanoclusters can be directly used as the contrast agent of ultrasonography and fluorescein angiography, at least.

Synthesis of Microbubbles

Figure 2:
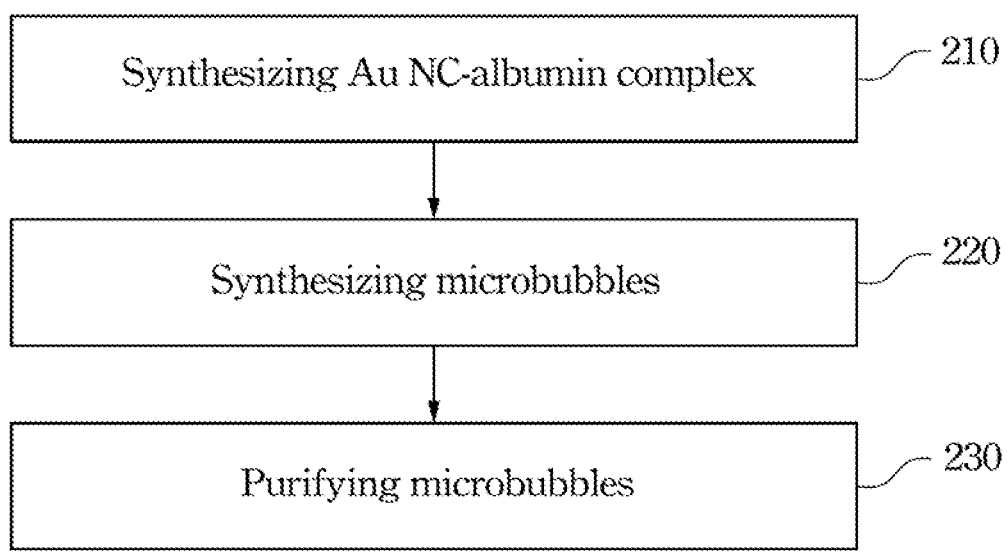
FIG. 2 is a process flow diagram of preparing microbubbles according to an embodiment of this invention.

FIG. 2 is a process flow diagram of preparing microbubbles according to an embodiment of this invention. In FIG. 2, the microbubbles can be prepared by the steps of synthesizing Au NC-albumin complex (step 210), synthesizing microbubbles (step 220), and purifying microbubbles (step 230). In step 210 of FIG. 2, the Au NC-albumin complexes can be AuNC@albumin or AuNC@ligand_albumin. Details about the steps above are discussed below.

Figure 3A:
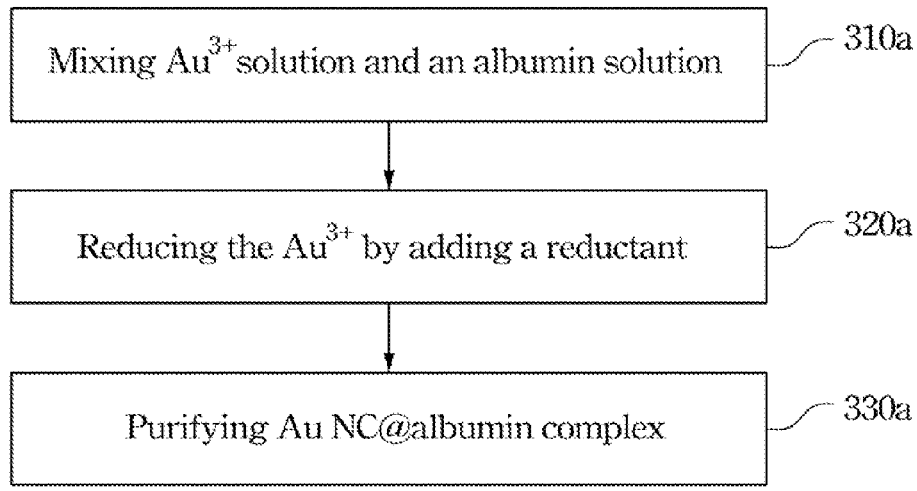
FIG. 3A is a process flow diagram of preparing 2-layer AuNC@albumin complex.

First, the Au NC-albumin complex is synthesized in step 210 in FIG. 2. FIG. 3A is a process flow diagram of preparing 2-layer AuNC@albumin complex. In step 310a of FIG. 3A, $Au^{3+}$ solution and an albumin solution with equal volume (such as 5 mL) are mixed and vigorously stirred for a period of time to form a mixing solution.

The $Au^{3+}$ solution can be aqueous solution of $HAuCl_4$, for example. The concentration of the $Au^{3+}$ can be 0.1-10 mM according to an embodiment of this invention. For example, the concentration of the $Au^{3+}$ can be 1-10 mM, or 5-10 mM. More specifically, the concentration of the $Au^{3+}$ can be 1, 2, 3, 4, 5, 6, 7, 8, 9, or 10 mM.

The albumin has been defined as above, and thus is omitted here. The concentration of the albumin can be 0.0758-0.7576 mM according to an embodiment of this invention. For example, the concentration of the albumin can be 0.1263-0.7576 mM or 0.4000-0.7576 mM. More specifically, the concentration of the albumin can be 0.4, 0.5, 0.6, 0.65, 0.7, or 0.75 mM.

In step 320a of FIG. 3A, a reductant, such as a base, is added into the mixing solution to form a reduced solution to obtain the Au NC-albumin complex with 2-layer structure. In order to reduce the impact on the pH value of the mixing solution, the added volume of the base solution is better less than 5% of the total volume of the mixing solution. Otherwise, a buffer agent will be needed. The reduced solution is then vigorously stirred for a period of time, such as 12 hours, to reduce the $Au^{3+}$ to fluorescent Au NC, and thus form Au NC@albumin complex. The base above can be NaOH or KOH, for example. The concentration of the base can be 1 N, and the added volume can be 0.5 mL when the added volumes of $Au^{3+}$ and albumin described above are both 5 mL, for example. If more ease to the subsequent purification and less impact to the applied human body is desired, NaOH is a better choice for the base.

In step 330a of FIG. 3A, the Au NC-albumin complex with 2-layer structure is purified. For example, the purification can be filtering by using a filter with 100 kDa pores or dialysis by using a semipermeable membrane to remove the unreacted $Au^{3+}$. The Au NC-albumin complex is then obtained by freeze drying.

Figure 3B:
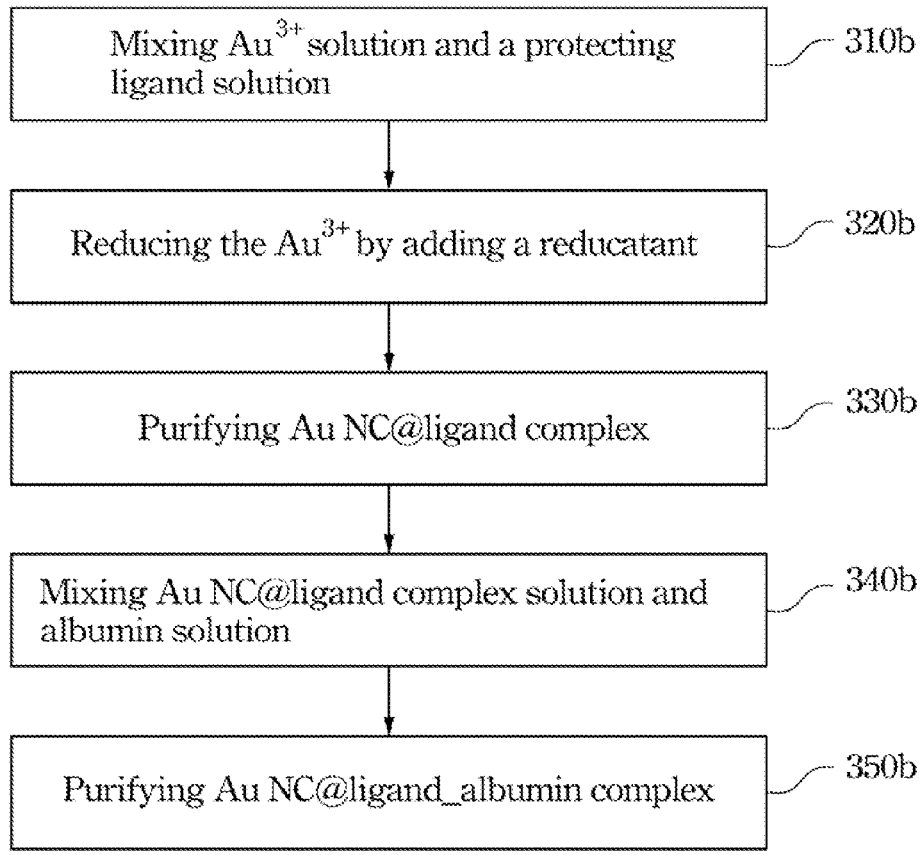
FIG. 3B is a process flow diagram of preparing 3-layer AuNC@ligand_albumin complex.

FIG. 3B is a first process flow diagram of preparing 3-layered AuNC@ligand_albumin complex. Steps 310b, 320b, and 330b in FIG. 3B are similar to the steps 310a, 320a, and 330b in FIG. 3A, except that the albumin in step 310b is replaced by a protecting ligand, and the reductant in step 320b may be another suitable reducing agent, rather than a base. Therefore, the details and the considerations of steps 310b, 320b, and 330b are omitted here.

Next, in step 340b of FIG. 3B, the Au NC@ligand complex obtained in step 330b and albumin are simply mixed in water or in phosphate buffered saline (PBS) to form Au NC@ligand_albumin complex.

The concentration of Au NC@ligand complex in the final solution can be 1-22 μM according to an embodiment of this invention. For example, the concentration of the added Au NC@ligand complex in the final solution can be 6-22 μM or 12-22 μM, for example. More specifically, the concentration of Au NC@ligand complex in the final solution can be 12, 13, 14, 15, 16, 17, 18, 19, 20, 21, or 22 μM, for example.

The concentration of the added albumin in the final solution can be 0.1516-0.9090 mM according to an embodiment of this invention. For example, the concentration of albumin in the final solution can be 0.3030-0.9090 mM or 0.6060-0.9090 mM, for example. More specifically, the concentration of albumin in the final solution can be 0.6060, 0.7578, 0.8333, 0.9090 mM, for example.

In step 350b of FIG. 36, the Au NC@ligand_albumin complex is purified. Similar to step 330a in FIG. 3A, the purification of step 350b can be filtering by using a filter with 100 kDa pores or dialysis by using a semipermeable membrane. The Au NC@ligand_albumin complex is then obtained by freeze drying.

Figure 4:
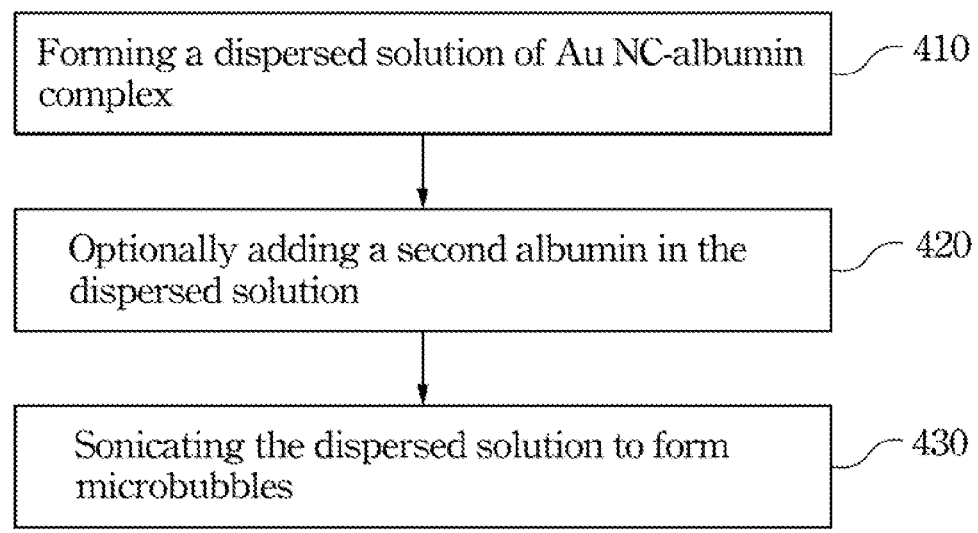
FIG. 4 is a process flow diagram of synthesizing microbubbles according to another embodiment of this invention.

Next, the microbubbles are synthesized in step 220 in FIG. 2. FIG. 4 is a process flow diagram of synthesizing microbubbles. In step 410 of FIG. 4, the obtained Au NC-albumin complex from the process of FIG. 3A or 3B is dispersed in water or PBS to form a dispersed solution. The concentration of the Au NC-albumin complex in the dispersed solution can be 40-60 mg/mL according to an embodiment of this invention. For example, the concentration of the Au NC-albumin complex in the dispersed solution can be 50-60 mg/mL or 55-60 mg/mL. More specifically, the concentration of the Au NC-albumin complex in the dispersed solution can be 40, 42, 44, 46, 48, 50, 51, 52, 53, 57, 55, 56, 57, 58, 59, or 60 mg/mL, for example.

Figure 3C:
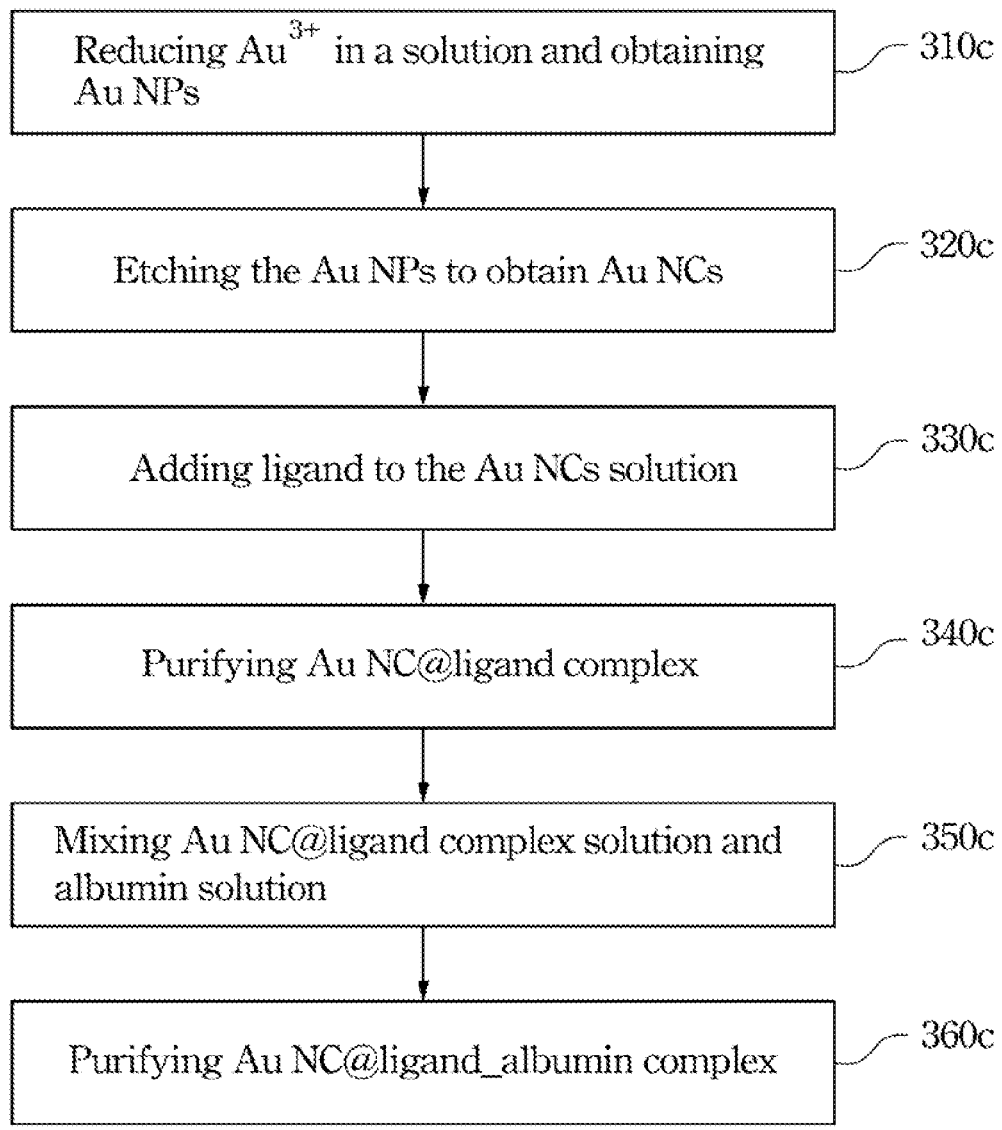
FIG. 3C is a second process flow diagram of preparing 3-layer AuNC@ligand_albumin complex.

FIG. 3C is a second process flow diagram of preparing 3-layer AuNC@ligand_albumin complex. In step 310c, $Au^{3+}$ is reduced by adding a reductant to the $Au^{3+}$ solution, and Au nanoparticles (abbreviated as NPs below) are thus formed in the solution. The concentration of the $Au^{3+}$ can be 0.25-25 mM according to an embodiment of this invention. For example, the concentration of the $Au^{3+}$ can be 0.25-25 mM, or 20-25 mM. More specifically, the concentration of the $Au^{3+}$ can be 0.25, 0.5, 0.75, 1, 5, 10, 15, 20, 2122, 23, 24, 25 mM.

In step 320c, further $Au^{3+}$ is added to etch the Au NPs to obtain Au NCs. The added amount of the $Au^{3+}$ can be 0.25-25 mM. For example, the added amount of the $Au^{3+}$ can be 20-25 mM.

In step 330c, a protecting ligand is added into the Au NCs solution to obtain Au NC@ligand complex. The ligand has been defined as above, and thus is omitted here. Next, since step 340c, 350c, and 360c are similar to step 330b, 340b, and 350b, the details are thus omitted here, too.

In step 420 of FIG. 4, a second albumin can be optionally added to the dispersed solution. When the complex is AuNC@albumin, the final molar ratio of the albumin/AuNC@albumin in the dispersed solution can be 1-4, 2-4, or 3-4, for example. When the complex is AuNC@ligand_albumin, the final molar ratio of the albumin/AuNC@ligand_albumin in the dispersed solution can be not greater than 1, 1/2, or 1/3, for example.

In step 430 of FIG. 4, the final dispersed solution is then sonicated by an ultrasound probe to form microbubbles. Then, the dispersed solution of the microbubbles is stayed for 1-3 minutes to stabilize the dispersed solution. The stabilized solution can be roughly delaminated into 3 layers. The lower layer mainly contains free Au NC-albumin complex. The middle layer mainly contains the microbubbles. The upper layer mainly contains larger bubbles.

The intensity of the ultrasound can be 11-24 watts according to an embodiment of this invention, and the diameter of the microbubbles can be 0.5-20 μm. For example, the intensity of the ultrasound can be 21-24 watts. More specifically, the intensity of the ultrasound can be 11, 13, 15, 17, 19, 20, 21, 22, 23, or 24 watts, for example. Only 1-3 minutes of sonicating time is enough. For example, the sonicating time can be 1, 1.5, 2, 2.5, or 3 minutes.

Finally, the obtained microbubbles are purified in step 230 in FIG. 2. The middle layer and the lower layer of the stabilized microbubbles solution is taken to be centrifuged later. The relative centrifugal force (RCF) in the centrifuging step is about 350. After centrifugation, the microbubbles are located in the upper layer. Hence, the upper layer is taken to obtain the microbubbles.

EMBODIMENT 1

Synthesis of AuNC@BSA Complex and Microbubbles Thereof

In this embodiment, AuNC@BSA complex was synthesized by the following steps.

5 mL of 10 mM $HAuCl_4$ solution was added into 5 mL of 50 mg/mL bovine serum albumin (BSA) solution, and then vigorously stirred at 37° C. for 2 minutes. 0.5 mL of 1 N NaOH was added into the mixed solution of the $HAuCl_4$ solution and the BSA solution, and then vigorously stirred for 12 hours at 37° C. to obtain gold nanoclusters and thus AuNC@BSA complex solution. Next, the solution of AuNC@BSA complex solution was filtered to remove unreacted gold ions and then freeze dried to obtain AuNC@BSA complex.

The photoluminescence data of AuNC@BSA complex are listed in Table 1 below. It can be seen that the excitation and emission data are the same for all examples in Table 1. Thus, it can be concluded that the relative amount of $HAuCl_4$ and BSA did not influence the photoluminescence property of the AuNC@BSA complex.

TABLE 1

| Photoluminescence data of AuNC@BSA complex | | | |
|---|---|---|---|
| $HAuCl_4$ (mM) | BSA (mg/mL) | Excitation (nm) | Emission (nm) |
| 0.1 | 0.5 | 260-500 | 550-750 |
| 1 | 5 | 260-500 | 550-750 |
| 10 | 50 | 260-500 | 550-750 |

Afterwards, the AuNC@BSA complex was dispersed in phosphate buffer solution to form a dispersed solution of AuNC@BSA complex. The dispersed solution of AuNC@BSA complex was then sonicated to form microbubbles of AuNC@BSA complex.

The photoluminescence of the microbubbles of AuNC@BSA complex are listed in Table 2 below. From Table 2, still, the photoluminescence property of the AuNC@BSA microbubbles was the same as the photoluminescence of the AuNC@BSA complex listed in Table 1 above. However, the sonication power can influence the size of the microbubbles. Except for the pure BSA microbubbles, the stronger the sonication power is, the larger the microbubbles' size is.

TABLE 2

| Photoluminescence of the microbubbles of AuNC@BSA complex | | | |
|---|---|---|---|
| Sonication power (watts) | Au@BSA*:BSA* (volume ratio) | Size (μm) | Emission (nm) |
| 11-13 | 1:1 | 1.753 ± 0.321 | 550-750 |
|  | 1:4 | 1.687 ± 0.296 | 550-750 |
|  | 0:1 | 1.854 ± 0.168 | N/A |
| 20-24 | 1:1 | 2.285 ± 0.631 | 550-750 |
|  | 1:4 | 3.226 ± 1.003 | 550-750 |
|  | 0:1 | 1.706 ± 0.552 | N/A |

*The concentration of both Au@ BSA and BSA was 55 mg/mL.

EMBODIMENT 2

Synthesizing AuNC@DHLA_BSA Complex and Microbubbles Thereof

In this embodiment, AuNC@DHLA_BSA complex was synthesized by the following step.

First, 0.625 mL of 100 mM decanoicaci was added into a 40 mL vial and then stirred. 1 mL of 25 mM tetrabutylammonium borohydride (TBAB), used as a reducing agent, and 0.8 mL of 25 mM $AuCl_3$ in 100 mM didodecyldimethylammonium bromide (DDAB) was added. The reaction was allowed to perform for about 10 minutes to from Au nanoparticles. Next, 25 mM of $AuCl_3$ in 100 mM DDAB was added into the Au nanoparticles solution to etch the Au nanoparticles for forming Au nanoclusters.

Subsequently, the solution of Au nanoclusters was added into the same volume of previous total solution of 200 mM lipoic acid in 50 mM tetrabutylammonium borohydride (TBAB) and then stirred for about 10 minutes. The lipoic acid is freshly reduced by TBAB added from the solution of Au nanoclusters to form dihydrolipoic acid (DHLA), and a complex of Au nanoclusters chelated by dihydrolipoic acid (noted as AuNC@DHLA below) was thus formed.

Next, the upper clean part of the AuNC@DHLA solution was removed. Then, methanol was added to dissolve the AuNC@DHLA again. The methanol solution of AuNC@DHLA was dried at a reduced pressure of 1 mbar. Chloroform was used to wash the AuNC@DHLA solid to remove organic residue. Methanol was reused again to dissolve the AuNC@DHLA. Finally, after remove the methanol, the AuNC@DHLA was dissolved in a buffered solution, having a pH value of about 9, of sodium borate and boric acid (abbreviated as SBB below) and then stayed in 55° C. for 24 hours. After ultracentrifugation, the resulting sample pellets are re-dispersed in PBS buffer. The resulted AuNC@DHLA can be excited at a wavelength of about 300-550 nm and emits at a wavelength of about 580-700 nm.

Afterwards, bovine serum albumin (BSA) was added into the dispersion solution of AuNC@DHLA in DPBS buffer to form 3-layer complex of AuNC@DHLA_BSA. Then, the dispersed solution was sonicated at 20-24 watts to form microbubbles. The photoluminescence data of the AuNC@DHLA_BSA microbubbles are listed in Table 3 below. From Table 3, the photoluminescence of the AuNC@DHLA_BSA complex, before and after microbubbles' formation, were the same. Therefore, the microbubbles' formation has no effect on the photoluminescence of the AuNC@DHLA complex.

TABLE 3 photoluminescence data of the AuNC@DHLA_BSA microbubbles

| AuNC@DHLA_BSA*:BSA* (volume ratio) | Size (μm) | emission (nm) |
|---|---|---|
| 1:0 | 2.200 ± 0.427 | 580-700 |
| 5:1 | 2.029 ± 0.222 | 580-700 |
| 0:1 | 1.706 ± 0.553 | N/A |

*The concentration of both Au@DHLA_BSA and BSA was 55 mg/mL.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:

1. A method of preparing microbubbles containing Au nanoclusters, comprising:
   mixing a $Au^{3+}$ solution and a first albumin solution to form a mixing solution;
   reducing $Au^{3+}$ by adding a base into the mixing solution to form a fluorescent Au nanocluster-albumin complex, wherein the Au nanocluster is protected by a layer of the first albumin;
   dispersing the Au nanocluster-albumin complex in water or phosphate buffered saline to form a dispersed solution;
   adding a second albumin in the dispersed solution; and
   sonicating the dispersed solution at a ultrasound intensity of about 11-24 watts for about 1-3 minutes to form microbubbles.

2. The method of claim 1, wherein the albumin is a serum albumin, an ovalbumin, or a storage albumin.

3. The method of claim 1, wherein the base is NaOH or KOH.

4. A method of preparing microbubbles containing Au nanoclusters, comprising:
   synthesizing fluorescent Au nanocluster-ligand complex having a structure of a Au nanocluster protected by a layer of the ligand;
   mixing a solution of the Au nanocluster-ligand complex and a solution of a albumin to form Au-albumin complexes, in which a layer of albumin surrounds each of the Au-ligand complexes;
   dispersing the Au nanocluster-albumin complex in water or phosphate buffered saline to form a dispersed solution;
   adding a second albumin in the dispersed solution; and
   sonicating the dispersed solution at a ultrasound intensity of about 11-24 watts for about 1-3 minutes to form microbubbles.

5. The method of claim 4, wherein the ligand is dihydrolipoic acid, glutathione, tiopronin, meso-2,3-dimercaptosuccunic acid, phenylethylthiolate, dodecanethiol, or mercaptoundecanol.

6. The method of claim 4, wherein the albumin is a serum albumin, an ovalbumin, or a storage albumin.

7. The method of claim 4, wherein the step of synthesizing Au nanocluster-ligand complex comprises:
   mixing a $Au^{3+}$ solution and a ligand solution to form a mixing solution; and
   reducing $Au^{3+}$ by adding a reductant into the mixing solution to form a plurality of Au nanocluster-ligand complexes.

8. The method of claim 4, wherein the step of synthesizing Au nanocluster-ligand complex comprises:
   reducing $Au^{3+}$ in a solution by adding a reductant to obtain Au nanoparticles suspending in the solution;
   etching the Au nanoparticles by adding further $Au^{3+}$ to the solution to obtain fluorescent Au nanoclusters; and
   adding a protecting ligand into the solution to obtain the Au nanocluster-ligand complex.

9. The method of claim 8, wherein the reductant comprises tetrabutylammonium borohydride (TBAB).

* * * * *